United States Patent [19]

Hart

[11] 4,382,074

[45] May 3, 1983

[54] SCINTILLATION PROXIMITY ASSAY

[76] Inventor: Hiram Hart, 3450 Wayne Ave., Bronx, N.Y. 10467

[21] Appl. No.: 175,132

[22] Filed: Aug. 4, 1980

Related U.S. Application Data

[63] Continuation-in-part of Ser. No. 890,325, Mar. 27, 1978, Pat. No. 4,271,139.

[51] Int. Cl.$^3$ .................. G01N 33/58; G01N 33/60
[52] U.S. Cl. .................................. 436/537; 436/804; 436/805
[58] Field of Search ................ 424/1, 12; 23/230 B

[56] References Cited

U.S. PATENT DOCUMENTS 4,271,139  6/1981  Hart ................................. 424/1

*Primary Examiner*—Christine M. Nucker
*Attorney, Agent, or Firm*—Holland, Armstrong, Wilkie & Previto

[57] ABSTRACT

An indirect, non-destructive, quantitative assay for the presence of antigens or antibodies in a biological fluid. The assay is based on the interfunctional behavior of a known biological material with the material whose presence is quantitatively sought. In the assay, the known biological material by a correlative action links two discreet interfunctional particles together within a zone of activation with one of the particles emitting light-pulses upon bombardment of electrons from the other particle within the zone of activation. Depending upon which presence is sought to be measured, i.e.; antigen or antibody, the detectable light-pulses give one measurement which gives the ultimate quantitative measurement of the presence of either an antibody or antigen in the biological fluid after their initial interfunctional behavior one to the other. The interfunctional behavior itself is conventional and known in the art.

12 Claims, 6 Drawing Figures

SCINTILLATION PROXIMITY ASSAY

BACKGROUND OF THE INVENTION

This is a continuation in part of United States application Ser. No. 890,325 filed Mar. 27, 1978, now U.S. Pat. No. 4,271,139.

In the standard latex fixation test (Singer Am. J. Med. 31, 766, 1961) an aqueous suspension of either antigen or antigen or antibody coated latex particles is employed. The concentration of antibody or antigen in an unknown sample is then estimated by the extent to which flocculation of the particles occurs as the result of antibody or antigen interparticulate bridging.

Since the concentration of antibody or antigen required for visible flocculation to occur is rather high, optical scattering assays have been developed both to improve the sensitivity of the general technique and to more effectively quantitate measurement (Gross et al U.S. Pat. No. 3,990,851 and Schulthess et al Immochem. 13, 1955, 1976). These methods require the use of specialized equipment and analysis. Moreover, their sensitivity appears to be limited to concentrations of antibody (or antigen) $\geq 5-10$ ngm/ml (Schulthess et al 1976). It is probable that this limitation in sensitivity arises from the difficulty in detecting light scattered from a relatively small number of dimers or trimers etc. against a background of the light scattered from a much larger number of monomers.

Optical techniques in which the formation of a fluorescence labelled antigen-antibody bond results either in quenching (Ullman U.S. Pat. No. 3,996,345) or in a shift in wave length of the fluorescent radiation (Ullman U.S. Pat. No. 3,998,943) have been devised. The technique depends upon the ability to prepare a suitable ligand-analog fluorescer having the desired emission properties for each assay, the sensitivity being limited in part by the extent to which the shifted and unshifted fluorescent radiation are present at the test wave length.

Radioimmunoassay (RIA) methods are generally considered to be inherently the most sensitive. A wide variety of techniques have been developed. Among the approaches most relevant to the invention here disclosed is that of solid phase RIA, originated by Catt and co-workers Biochem. J. 100: 31c (1966) and applied in a variety of ways. In one variation of this approach a known amount of antibody or antigen is first bound to a solid material - powder, plastic tube or disc. The sample solution to be tested containing an unknown quantity of the corresponding antigen or antibody as well as a known amount of labelled antigen or antibody is incubated in contact with the solid material. After incubation, the solution is then appropriately removed and the fraction of radioactively labelled antigen or antibody remaining bound to the solid material determined. From considerations of competitive binding the unknown concentration of the unlabelled antigen or antibody present in the sample being tested can be found. Although RIA is very sensitive, the procedures involved in separating bound from unbound fractions are not always simple and generally result in irreversibly altering the sample being tested. It follows that RIA is not ideally suited, for assaying the same sample repeatedly as in studying binding kinetics, nor for straightforward clinical determinations in which convenience is a major consideration.

Summarizing then, the latex fixation tests are less sensitive but more convenient; RIA is more sensitive but less convenient.

SUMMARY OF THE INVENTION

In its general form, the invention is a 6 component system consisting of:
(a) Initiator, (b) Exciter, (c) Absorber, (d) Responder, (e) Transducer, and (f) Detector which is designed to measure the distribution of spatial separations of two distinct types of elements A and B.

The initiator, which may be an external source of particulate radiation or of electromagnetic radiation of wave length $\lambda_1$ causes the exciter on an element of Type A to emit a burst of fluorescent radiation of wave length $\lambda_2 > \lambda_1$. A fraction of the radiation of wave length $\lambda_2$ attenuated as a result of its passage through the medium containing a material tending to selectively absorb $\lambda_2$ arrives at the responder on an element of Type B. The responder in turn selectively reacting to the radiation from the Type A element emits fluorescent radiation of wavelength $\lambda_3 > \lambda_2$ which is either wave shifted in turn by the transducer or measured directly by the detector. From the distribution in the intensities of the pulses of radiation arriving at the detector information as to the distribution of inter-element spatial separations can be obtained. The average intensity of detected radiation or equivalently the number of pulses of radiation detected per unit time can also be used to measure the extent of Type A - Type B proximity. If the Type A elements are in the form of one group of particles and the Type B elements are a second group of particles, then the intensity of radiation or the pulses detected per unit time can be used to measure the extent of Type A-Type B dimer and larger aggregate formation.

In an embodiment of the invention already tested, the initiator and exciter are combined in the form of tritiated latex particles while the responder-transducer function is carried out by commercially available polystyrene scintillant particles. Since the average range of $^3H \beta$ rays in water is only $\sim 1\mu$, any aqueous medium in which the two types of particles are suspended can serve as an effective absorber. Detection is readily carried out with a standard liquid scintillation counting system energy gated for tritium counting.

Either but not both of the elements A or B can also take the form of test tubes, vials, slides, fibers etc. For example the sample containers or slides can be fabricated of a plastic scintillant and so serve as a combined responder-transducer. Alternatively, tritium or other relatively long lived and short range $\beta$ emitting or $\alpha$ emitting isotopes can be appropriately incorporated within the walls of a test tube or other container or an immersible element in the medium to serve as a safe and effective combined initiator and exciter which can be used for repeated assays.

A basic advantage of this invention over prior immuno-assay techniques is that on the one hand neither the antigen nor the antibody molecules need be labelled or specially processed and on the other hand that the previous limit on sensitivity of the mechanical amplification of the latex fixation test no longer applies. A single antigen-antibody-antigen bond serving as an inter-particulate bridge can link together millions of potentially interacting molecules. Since the same two particulate types can be used for essentially all immuno-assays (some of their surface characteristics may have to be adapted) many different assays can be performed with essentially the same equipment and using the same procedures.

BRIEF DESCRIPTION OF THE DRAWINGS

The operation of the assay systems and benefits that may be derived from the invention may be better understood through reference to the following description of embodiments and related drawings.

DESCRIPTION OF THE PREFERRED EMBODIMENTS

Figure 1:
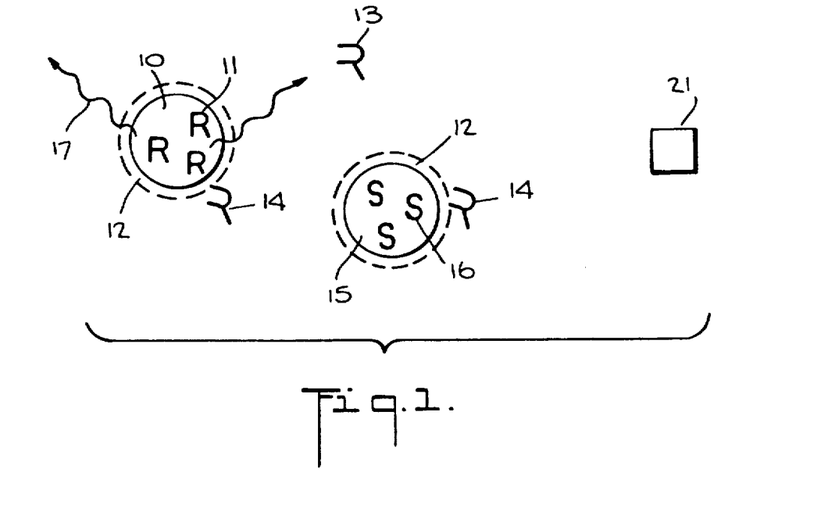
Figure 2:
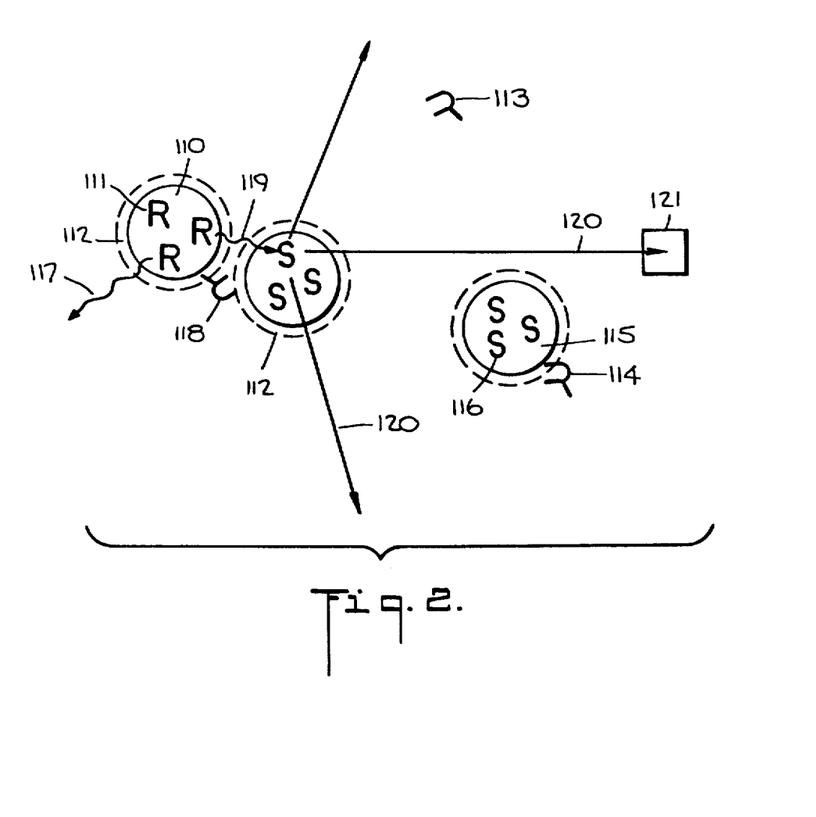

In the accompanying FIGS. 1. & 2., Type A particles, 10 and 110, are represented as suspended in a solution. The tracer atoms 11 and 111 are $\alpha$ ray or short range $\beta$ ray emitting nuclides strongly attached to the particles, preferably but not necessarily on the surfaces. An antigen coating (or antibody coating) 12 or 112 is bound, preferably covalently, to the surfaces of the particles. The reactant under assay is represented as 13 or 113 if unattached to a particle and as 14 or 114 if attached to one or possibly two Type A particles. The arrows 17 and 117 represent $\alpha$ or $\beta$ rays emitted by the radioactive tracer atoms 11 and 111 whose paths terminate in the solution and do not give rise to any signal at the detector 21 or 121.

Type B particles, 15 and 115, are also coated with the same antigen (or antibody) 12 or 112, but instead of being coated with radioactive atoms as well, they incorporate radiation sensitive materials 16 and 116, preferably but not necessarily distributed throughout their volume, which scintillate upon radiation exposure. For effective measurement the radius of type B particles should usually but not necessarily be of the order of magnitude of the mean range of the $\alpha$ ray or $\beta$ ray path length in water and the type B particle material.

Depending upon the concentration of reactant, and the conditions of incubation, a variable number of Type A and Type B particles will be linked by antibody bridges 118 (or antigen bridges provided more than one active site per antigen exists). Since the mean path lengths 17 or 117 can be chosen, by appropriate selection of the radioisotope, to be significantly larger than the antigen-antibody-antigen extended length or the antibody-antigen-antibody extended length, $\alpha$ rays or $\beta$ rays 119 from Type A particles will initiate scintillations within the Type B particles resulting in photons 120 arriving at the detector 121. For dilute suspensions of a mixture of Type A and Type B particles, the probability of scintillations is very much enhanced by dimer and higher order aggregation over that which would occur in a randomly dispersed monomer system. Thus the number of scintillation photons arriving at the detector is a measure of the amount of aggregate formation and therefore of the concentration of reactant. If the antigen being assayed has only one active site for a given antibody (i.e. derived from a given species), the Type A particles can be coated with one antibody and the Type B particles with another antibody derived from a different species and binding to a different site on the antigen. In such a system, the antigen will only form bridges between unlike particles further improving the effectiveness of SPA. In any event, the entire intact sample can be non-destructively assayed repeatedly in contrast to optical scattering methods which usually analyse only a small fraction of the sample at a time or RIA which usually involves separative sample altering procedures.

SPA therefore provides a very sensitive and direct assay of antigen and antibody concentrations as well as a very convenient technique for studying particulate binding characteristics as a function of time and experimental conditions. Moreover, no special equipment is likely to be required since liquid scintillation counting systems are now standard laboratory equipment.

Although the above described embodiment using a mixture of tritiated particles and scintillant particles is very sensitive, simple to carry out, and has been successfully tested, SPA does not depend inherently upon the use of radioisotopes.

As an alternative embodiment based on the foregoing, both groups of particles can be coated with an antigen, when it is desired to test for the presence of antibody. However, if free antigen is added to the fluid medium, and it reacts with the free antibody already in the fluid medium, you could also measure the amount of antigen added to the system by a drop in the measurement of light-pulses. Yet, in this situation, you are still using antigen-coated particles, the reading will be of the amount of antibody left in the system, but it can be correlative to the amount of antigen which reacted with the free antibody. In other words, one reading, but two measurements, viz. antibody and antigen.

In some cases, for exceptional results, the liquid medium should be aqueous, the Ph should be in the range of 6 to 9, and the temperature of the medium should be about 5° C. to 40° C. and the antibody should be present at a concentration of about $10^{-5}$ to $10^{-12}$M. if you are going to measure for antigens.

In other words, the proximity of the particles is measured; when they are within the activation range, a light-pulse is given off. This is a direct measurement of the biological-linking material between the particles. However, if some biological-linking was removed from its interaction with the coated particles, you would get a drop in reading. You would be still measuring the number of light-pulses brought about by the linking of the discrete particles within the activation range by the biological-linking material, and therefor the amount of linking material is directly measured.

However, continuing, the latter measurement can be indirectly quantitatized to give a measurement of a material which by interaction, removed the biological-linking material before it could enter the zone of activation of the discrete particles. It should be emphasized that we are measuring detectable signals which are distinguishable from that which might occur if the differing types of particles were not within the range of activation. In other words, a direct reading of the amount of material under analysis can be made by this system. But, also the same reading could be indirectly indicative of a second material in such system. This is usually possible when the second material is also of the class of material that is used to coat the particles for use in the direct process. One measurement of light-pulse, and you have a measurement of two different materials. In immunological systems, these are both antigens and antibody.

Figure 3:
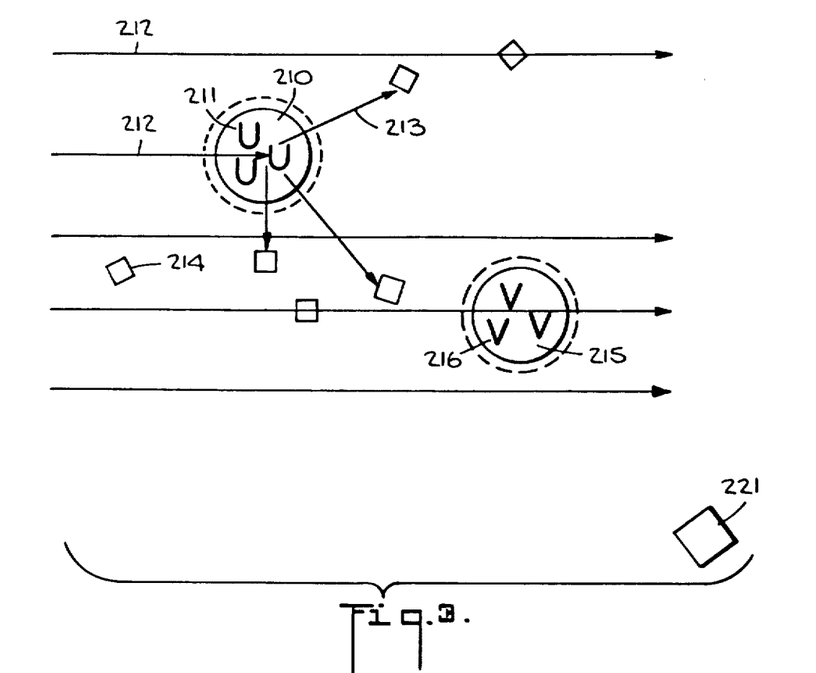

In the accompanying FIGS. 3. & 4., Type A particles 210 and 310 containing a fluorescent material 211 and 311 are represented as suspended in a solution. A beam from an external source of electromagnetic radiation 212 and 312 of wave length $\lambda_1$ is incident upon the system. The incident radiation causes the fluorescent material 211 and 311 to emit electromagnetic radiation 213 and 313 in a band of wave lengths centered about $\lambda_2 > \lambda_1$. In the absence of reactant as in FIG. 3, relatively little particulate aggregation will occur and in sufficiently dilute suspensions, the radiation 213 will be rapidly attenuated by the dye 214 chosen to be transparent to $\lambda_1$ and to very effectively absorb radiation in the $\lambda_2$ band. In the presence of reactant 317 and 320 as in FIG. 4, however, dimer and higher order particulate aggregation occurs resulting in Type A and Type B particles 215 in close proximity. The fluorescent material 216 and 316 in the Type B material is chosen so that it will not interact with $\lambda_1$ wave length radiation but will fluoresce in a band about $\lambda_3$ when exposed to radiation in the $\lambda_2$ band. If the dye material 314 is chosen to satisfy the further condition that it is transparent to the Type B particle fluorescence radiation (i.e. the $\lambda_3$ band), the fluorescent events in the Type B particles will result in photons 318 in their characteristic band of wave lengths about $\lambda_3$ arriving at the detector 321. The extent to which the reactant results in dimer and higher order aggregation can therefore be inferred (or determined by comparison with standard curves) by the intensity of the $\lambda_3$ band radiation arriving at the detector 321.

The fluorescent materials can comprise dyes and appropriately doped crystals and glasses etc. Moreover the particles themselves can be composite with appropriate filters on their surfaces and the fluorescent material in their interior to improve their stimulus response characteristics.

Figure 4:
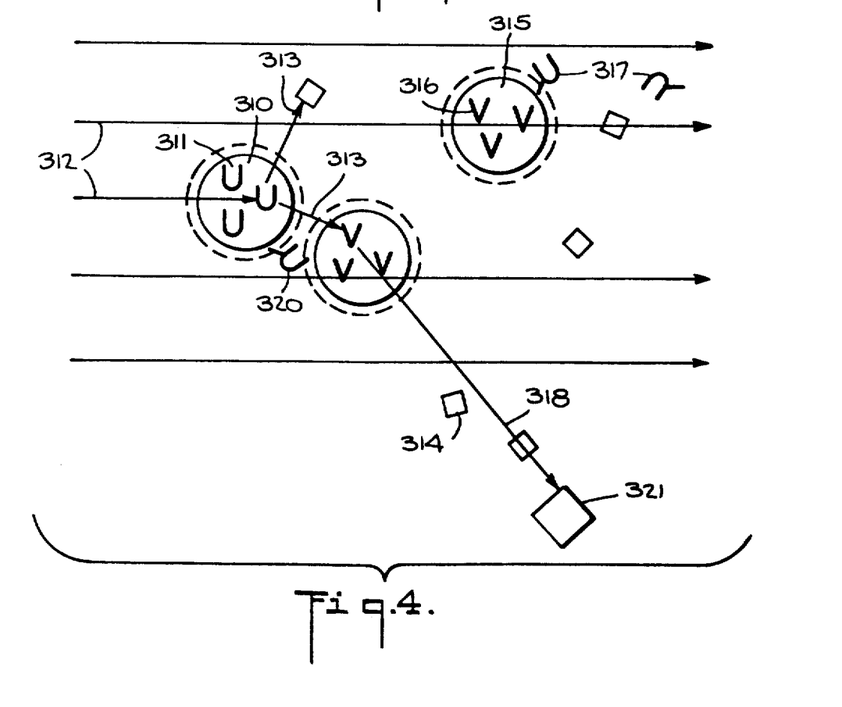

The system can be characterized as a fluorescent "ladder" $\lambda_1 \rightarrow \lambda_2 \rightarrow \lambda_3 \rightarrow$ Detector, where the incident $\lambda_1$ radiation does not interact directly with the Type B particles and the dye 314 is selected to strongly absorb in the $\lambda_2$ region and to be transparent to the $\lambda_1$ and $\lambda_3$ bands.

Figure 5:
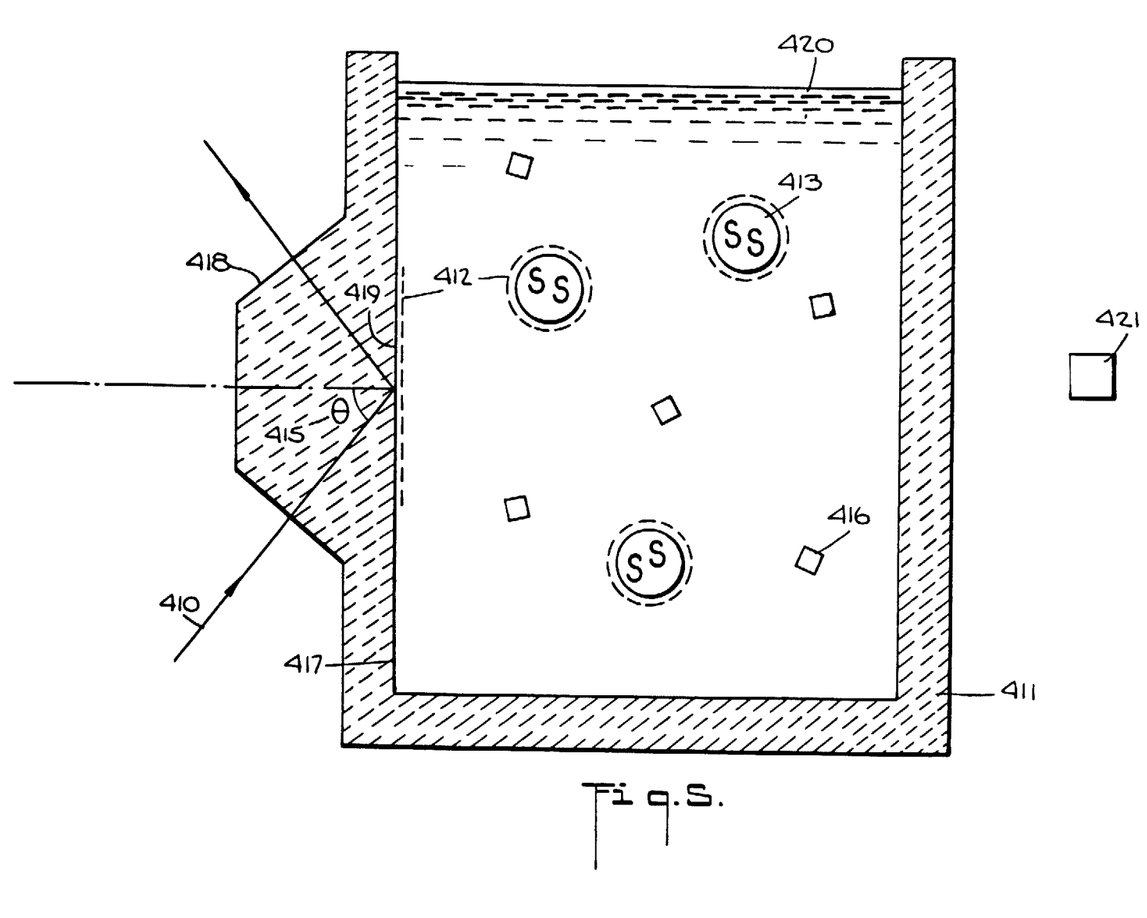
Figure 6:
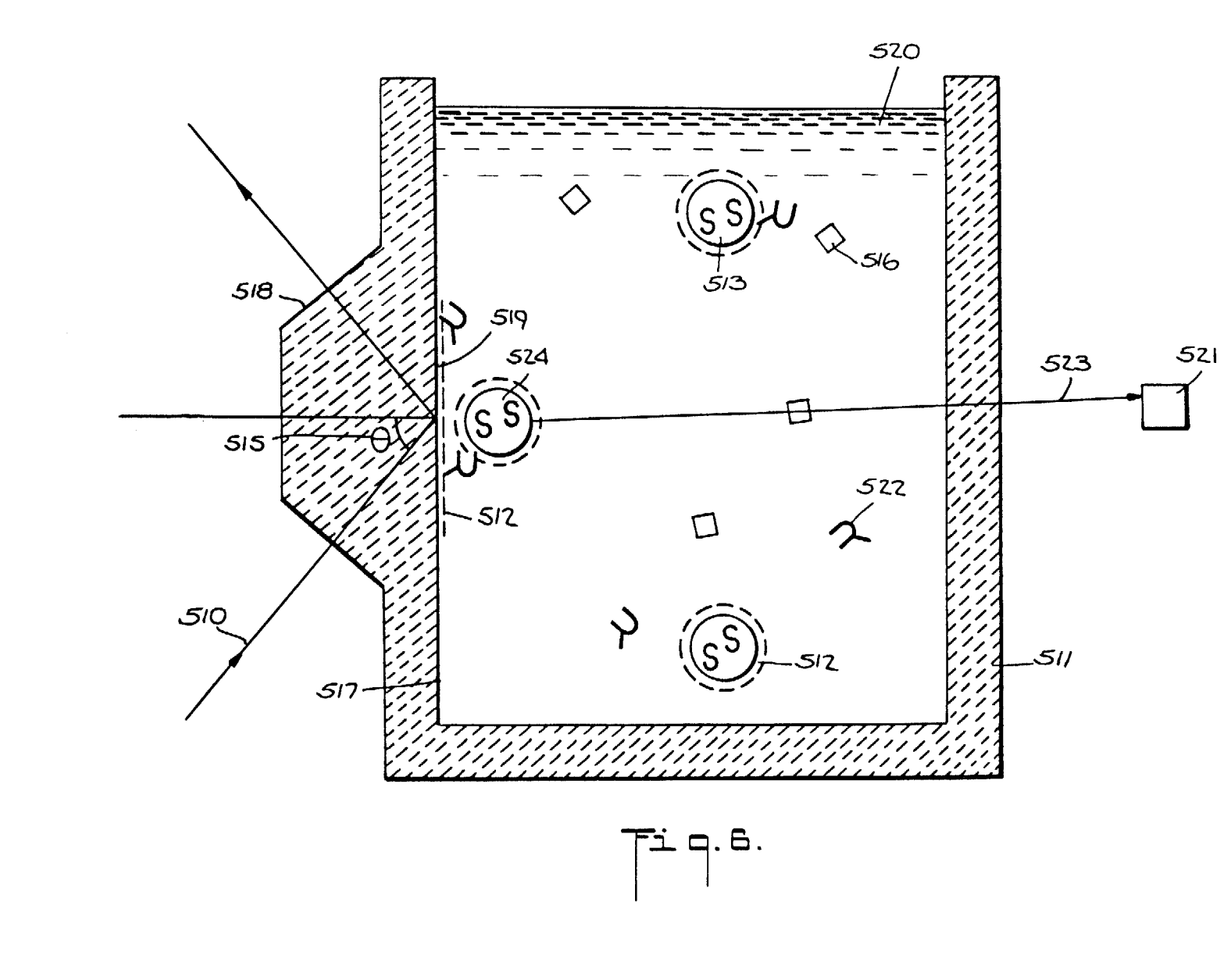

A variation of SPA in which only one class of scintillant particles is required is diagrammed in FIGS. 5 and 6. A beam of electromagnetic radiation 410 of wave length $\lambda_1$ is incident upon the transparent container 411 and strikes the wall of the container 417 at an angle $\theta$, 415 greater than the critical angle. As is well known from the simple theory of geometrical optics, the beam experiences a complete internal reflection at the interface 419 between the container 411 and the solution 420. However, it is also known from the more advanced theory of physical optics that the radiation field of beam 410 actually extends past the interface 419 and into the solution 420 to a depth of several wave lengths. If the interface 419 has an antigen coating 412 that does not fluoresce under exposure to radiation of wave length $\lambda_1$, this short range penetration has little effect, however, and no signal will arrive at the detector 421 unless one of the scintillant particles 413 just happens to be within the penetration distance. The effect of any residual radiation of wave length $\lambda_1$ entering the solution 420 from surface imperfections, interface scattering from the antigen coating 412, and the reflection at 418 can be minimized by adding dye molecules 416 to the solution which strongly absorb radiation of wave length $\lambda_1$.

If antibody 522 is present in the system as diagrammed in FIG. 6, scintillant particles 524, will be bound to the interface 519. Since the extended lengths of the antigen-antibody-antigen bond or conversely the antibody-antigen-antibody bond are both less than $\sim 1000$ A, the radiation field of wave length $\lambda_1$ penetrating the solution can now interact with the surface bound particles 524 to produce fluorescent radiation of longer wave length $\lambda_2 > \lambda_1$ to which the dye molecules 516 are essentially transparent. Some of the resulting $\lambda_2$ photons 523 will arrive at the detector 521 and so provide a measure of the number of surface bound scintillant particle 524 and therefore of the antibody concentration. To improve the efficiency of detection of the $\lambda_2$ photons, photons, reflective coatings can cover the non-operative sides of the solution chamber (i.e. a reflective coating everywhere except on the interface area 519 and the area in the field of view of the detector).

The actual interface 519 may make use of a replaceable element such as a slide. Alternatively, the interface 519 can be the surfaces of slides, foils or fibers which are dipped into or pass through the solution 520, the incident light entering and principally exiting the system through the ends or edges of the slides, foil or fibers as in fiber optics applications. The entering and exiting $\lambda_1$ radiation not involved in interaction with surface bound particles 524 would of course, be appropriately shielded or otherwise prevented from directly irradiating solution 520.

EXAMPLE 1

Preparation of Phosphate Buffer:
Sol. A. 3.2 gms $NaH_2PO_4.H_2O/100$ ml $H_2O$
Sol. B. 5.3 gms $NA_2HPO_4.7H_2O/100$ ml $H_2O$ Conc. Buffer: 16 ml Sol. A. + 84 ml Sol. B.
Phosphate Buffer: 1 part Conc. Buffer + 3 parts $H_2O$. adjust pH with NaOH to $\sim 8.5$.

Preparation of Solution C.
4.21 gms CsCl + 0.5 ml 2% Thimerosal in $H_2O$ + 10 ml Phosphate Buffer + $H_2O$ to raise to 100 ml + NaOH to adjust pH to $\sim 8.5$.

Preparation of L*.
Mix: 50 mgm of Ne102 Scintillant Particles $1\mu \sim 10\mu$ diam obtained from Nuclear Enterprises + 2 mgm of Poly DL-Alanine 71-102 obtained from Miles + 1 ml 2% $HNO_3$ in $H_2O$.
Slurry mixture in mortar & pestle for $\sim \frac{1}{2}$ hour.
Add 10 cc 2% $HNO_3$ to mixture and transfer to capped glass vial.
Sonicate for 3 minutes.
Place vial in incubator @37° C. for $\sim 5$ hours.
Sonicate for 2 minutes.
Replace in incubator @37° C. for $\sim 12$ hours.
Refrigerate @4° C. for $\sim 5$ hours.
Spin @ $\sim 3000$ rpm for 5 min. Discard supernatant
Resuspend particles in $H_2O$.
Spin @ $\sim 3000$ rpm for 5 min. Discard supernatant.

Precipitate Particles Labelled L*-I.

To $\sim 40$ mgm L*-I (i.e. $\sim 90$% of I.) add 1 mgm HSA in 0.05 ml phosphate buffer. Mix for $\sim 3$ min and add 5 ml phosphate buffer.
Spin at 3000 rpm for 20 min. Discard Supernatant To $\sim 0.2$ ml precipitate + fluid - add 10 mgm CBDD in 0.5 ml $H_2O$ (CBDD-PIERCE No. 22980). Sonicate for 30 seconds.
Add 0.5 ml $H_2O$ containing 10 mgm HSA slowly over 10 min. while shaking gently. Sonicate for 1 min.

Leave overnight in refrig. @4° C. on an intermittant roller ($\sim 5$ mins. motion every 2 hours - 2 rotations/min when operative).

Raise to 5 ml with phosphate buffer ph 8+.
Spin 2X @12,000 rpm for 20 min each in phosphate buffer.
Discard Supernatants.
Raise to 5 ml with 1% Goat Serum in phosphate buffer.
Spin 1X @12,000 rpm for 20 min. Discard Supernatant
Add 3 ml - 1% G.S. in phosphate buffer - and place in Refrig.
read for use in Assay. L*-II.
Preparation of Tritiated Latex Particles (LH):
Tranship 4 ml aliquot of a 10% suspension of carboxylate surface modified $0.926\mu$ diam. Dow polystyrene particles to New England Nuclear for tritiation by the Wilsbach procedure.
Conditions adjusted (i.e. time of exposure and amount of $^3H$ used) to result in a satisfactory specific activity (80 mc/400 mgm can be used).

Remove 0.2 ml of tritiated particles from the reconstituted suspension of 400 mgm in 10 ml as received from New England Nuclear ($\sim$8 mgm particles and 1.6 mc $^3H$).

Add 2 of phosphate buffer to the particles and dialyse v.s. phospate buffer for 48 hours at 4° C.

Add 5 ml phosphate buffer to the particles after dialysis and spin for $\sim$30 @3000 rpm. Discard supernatant. Repeat once.

Add 0.5 ml $H_2O$. Particles labelled - LH-III.

To $\sim$6 mgm of the particles LH-III in $\sim$0.5 ml $H_2O$ add 4 mgm CBDD in 0.2 ml $H_2O$ (CBDD solution freshly prepared). Add 2 mgm of Human Serum Albumin. in 0.1 and $H_2O$ slowly over 10 minutes while shaking gently. Sonicate for 1 min. Leave overnight in refrigerator at 4° C. on an intermittent roller ($\sim$5 minutes motion every 2 hours - $\sim$2 rotations/min. when operative).

Raise to 5 ml with phosphate buffer Spin 2X at 12,000 rpm for 20 min. each Discard supernatants Raise to 5 ml with 1% Goat Serum in phosphate buffer. Spin at 12,000 rpm for 20 min. Discard supernatant.

Add 3 ml - 1% G.S. in phosphate buffer and place in refrigerator.
Label LH-IV.

To 285 ml of solution C on a magnetic stirrer add 15 ml freshly thawed Goat Serum. Add $\sim$150$\mu$ gm of L*-II in $\sim$0.02 ml (supernatant material remaining suspended after being mixed and left for $\sim$24 hours in refrigerator).
Resuspend LH-IV thoroughly - syringe repeatedly through a #25 needle and add $\sim$50$\mu$ gm in $\sim$0.05 ml to solution C above.
Fill 32 liquid scintillation vials with 8 ml each of above solution.
Add Rabbit anti-human albumin antisera to the vials in quadruplicate at titers of $10^{-3}$, $10^{-4}$, $10^{-5}$, $10^{-6}$, $10^{-7}$, $10^{-8}$, control.

Results after 24 and 48 hours of incubation at room temperature. Each value is the average CPM for 4 samples counted 10 minutes each.

| Time | Titers | | | | | | |
|---|---|---|---|---|---|---|---|
| | 1 $10^{-3}$ | 2 $10^{-4}$ | 3 $10^{-5}$ | 4 $10^{-6}$ | 5 $10^{-7}$ | 6 $10^{-8}$ | 7 Control |
| 24 hours | 1780 | 1643 | 722 | 271 | 245 | 244 | 246 |
| 48 hours | 2045 | 2036 | 1173 | 256 | 201 | 192 | 194 |

24 hours Student $t_{4-7} = 3.14$ ⎫ Significant at level of $\alpha > 0.05$.
48 hours Student $t_{4-7} = 5.12$ ⎭
24 hours Student $t_{5-7} = 0$ ⎫ Not Significant
48 hours Student $t_{5-7} = 0.6$ ⎭

EXAMPLE 2

To 285 ml Solution C add 30 mgm of D-L-Polyalanine
Add $\sim$150$\mu$ gm of L*-II
Add $\sim$150$\mu$ gm of LH-III
Fill 32 vials with 8 ml each
Add Rabbit anti-human alumin anti-sera to the vials
Incubate at room temperature.
Results after 22 and 31 hours:

| Time | Titers | | | | | | |
|---|---|---|---|---|---|---|---|
| | 1 $10^{-3}$ | 2 $10^{-4}$ | 3 $10^{-5}$ | 4 $10^{-6}$ | 5 $10^{-7}$ | 6 $10^{-8}$ | 7 Control |
| 22 hours | 603 | 680 | 724 | 836 | 935 | 961 | 974 |
| 31 hours | 590 | 665 | 686 | 821 | 937 | 955 | 968 |

22 hours Student $t_{4-7} = 8.36$ ⎫ Significant at level at $\alpha > 0.05$.
31 hours Student $t_{4-7} = 9.76$ ⎭
22 hours Student $t_{5-7} = 2.4$ ⎫ Possibly significant
31 hours Student $t_{5-7} = 1.8$ ⎭

Note that the dependence of the counts upon the titer is reversed from that in example 1. Although homogeneous (L*) (L*) aggregation would tend to decrease counts, this is also probably in part the result of non-specific binding by small concentrations of sera as further displayed in example 3.

EXAMPLE 3

To 285 ml Solution C add 30 mgm of D-L-Polyalanine
Add $\sim$150$\mu$ gm of L*-II
Add $\sim$150$\mu$ gm of LH-III
Fill 32 vials with 8 ml each
Add freshly thawed goat serum to the vials at the indicated titers.
Incubate at room temperature.
Results after 18 and 32 hours

| Time | Titers | | | | | | |
|---|---|---|---|---|---|---|---|
| | 1 $10^{-3}$ | 2 $10^{-4}$ | 3 $10^{-5}$ | 4 $10^{-6}$ | 5 $10^{-7}$ | 6 $10^{-8}$ | 7 Control |
| 18 hours | 456 | 552 | 612 | 707 | 795 | 795 | 813 |
| 32 hours | 425 | 508 | 575 | 683 | 791 | 800 | 814 |

18 hours Student $t_{4-7} = 6.5$ ⎫ Significant at level of $\alpha > 0.05$.
32 hours Student $t_{4-7} = 9.27$ ⎭
18 hours Student $t_{5-7} = 1.58$ ⎫ Possibly significant -continued

| | Titers | | | | | | |
|---|---|---|---|---|---|---|---|
| | 1 | 2 | 3 | 4 | 5 | 6 | 7 |
| Time | $10^{-3}$ | $10^{-4}$ | $10^{-5}$ | $10^{-6}$ | $10^{-7}$ | $10^{-8}$ | Control |
| 32 hours Student $t_{5-7}$ = 1.53 | | | | | | | |

Note that the presumably non-specific binding of the goat serum can thus be measured at very low concentrations - a result also obtained using L*-II with LH-IV, L*-I with LH-IV and L*-I with LH-III.

I claim:

1. In an improved non-destructive method of biological fluid assay wherein antibodies link antigen-coatings on fluid suspensions of both a plurality of tritiated-particulates and potentially scintillating-particulates within activating range one to the other, each of said linked scintillating-particulates emitting detectable light-pulses upon activation responsive to bombardment of energy from each of said linked tritiated-particulates within said range, said detectable light-pulses initially measured correlatively to the amount of said antibody in said fluid, the improvement wherein of adding a known amount of said antigen-coated tritiated particulates and said antigen-coated scintillating particulates to said fluid, measuring the resulting detectable light-pulses and correlating the reduction in measured light-pulses from said initially measured light-pulses to the reduction in the amount of antibodies in said fluid linked to said two particulates, and this being correlative to the amount of unbound antigens initially available in said fluid.

2. The method of claim 1 wherein said fluid is an aqueous medium having a pH in the range of about 6 and about 9, the temperature of said medium is between about 5° C. and about 40° C., and the concentration of available antibodies in said medium is between about $10^{-5}$ M and about $10^{-12}$ M.

3. In an improved non-destructive method of biological fluid assay wherein antigens link antibody-coatings on fluid suspensions of both a plurality of tritiated-particulates and potentially scintillating-particulates within activating range one to the other, each of said scintillating particulates emitting detectable light-pulses upon activation responsive to bombardment of energy from each of said linked tritiated-particulates within said range, said detectable light-pulses initially measured correlatively to the amount of said antigens in said fluid, the improvement wherein of adding a known amount of said antibody-coated tritiated particulates and said antibody-coated scintillating particulates to said fluid, measuring the resulting detectable light pulses and correlating the reduction in measured light-pulses from said initially measured light-pulses to the reduction in the amount of antigens in said fluid linked to said two particulates, and this being further correlative to the amount of unbound antibodies initially available in said fluid.

4. The method of claim 3 wherein said fluid is an aqueous medium having a pH in the range of about 6 and about 9, the temperature of said medium is between about 50° C. and about 40° C., and the concentration of said available antigens in said fluid medium is between $10^{-5}$ and about $10^{-12}$ M.

5. In an improved non-destructive method of biological fluid assay wherein antibodies link antigen-coated tritiated-solid-phase materials to antigen-coated potentially scintillating-solid-phase materials within activating range one to the other, said scintillating-solid-phase materials being particulates and emitting detectable light-pulses upon activation responsive to bombardment of energy from said linked solid-phase-tritiated materials within said range, said detectable light-pulses initially measured correlatively to the amount of said antibody in said fluid, the improvement wherein of adding a known amount of said antigen-coated potentially scintillating particulates to said fluid, measuring the resulting detectable light-pulses and correlating the reduction in measured light-pulses from said initially measured light-pulses to the reduction in the amount of antibodies in said fluid linked to said two antigen-coated materials, and this being correlative to the amount of unbound antigens initially available in said fluid.

6. The method of claim 5 wherein said fluid is an aqueous medium having a pH in the range of about 6 and 9, the temperature of said medium is between about 5° C. and about 40° C., and the concentration of said available antibodies in said fluid medium is between about $10^{-5}$ M and about $10^{-12}$ M.

7. In an improved non-destructive method of biological fluid assay wherein antigens link antibody-coated tritiated solid-phase materials to antibody-coated potentially scintillating-solid-phase materials within activating range one to the other, said scintillating-solid-phase materials being particulates and emitting detectable light-pulses upon activation responsive to bombardment of energy from said linked tritiated-solid-phase-materials within said range, said detectable light-pulses initially measured correlatively to the amount of said antigens in said fluid, the improvement wherein of adding a known amount of said antibody-coated, potentially scintillating-particulates to said fluid, measuring the resulting detectable light-pulses and correlating the reduction in measured light-pulses from said initially measured light-pulses to the reduction in the amount of antigens in said fluid linked to said antibody-coated materials, and this being correlative to the amount of unbound antibodies initially available in said fluid.

8. The method of claim 7 wherein said fluid is an aqueous medium having a pH in the range of about 6 and about 9, the temperature of said medium is between about 5° C. and about 40° C., and the concentration of said available antigens in said fluid medium is between about $10^{-5}$ M and about $10^{-12}$ M.

9. In an improved non-destructive method of biological fluid assay wherein antibodies link antigen-coated tritiated-solid-phase materials to antigen-coated potentially scintillating-solid-phase materials within activating rante one to the other, said tritiated-solid-phase materials being particulate and said scintillating solid-phase-materials emitting detectable light-pulses upon activation responsive to bombardment of energy from said linked tritiated-particulates within said range, said detectable light-pulses initially measured correlatively to the amount of said antibody in said fluid, the improvement wherein of adding a known amount of said antigen-coated tritiated-particulates to said fluid, measuring the resulting detectable light-pulses and correlating the reduction in measured light-pulses from said initially measured light-pulses to the reduction in the amount of antibodies in said fluid linked to said two antigen-coated materials, and this being correlative to the amount of unbound antigens initially available in said fluid.

10. The method of claim 9 wherein said fluid is an aqueous medium having a pH in the range of about 6 and about 9, the temperature of said medium is between about 50° C. and about 40° C., and the concentration of said antibodies is between about $10^{-5}$ M and about $10^{-12}$ M.

11. In an improved non-destructive method of biological fluid assay wherein antigens link antibody-coated tritiated-solid-phase materials to antibody-coated potentially scintillating-solid-phase materials within activating rante one to the other, said tritiated-solid-phase materials being particulates and said scintillating solid-phase materials emitting detectable light-pulses upon activation responsive to bombardment of energy from said linked tritiated-particules within said range, said detectable light-pulses initially measured correlatively to the amount of antigens in said fluid, the improvement wherein of adding a known amount of said antibody-coated tritiated-particulates to said fluid, measuring the resulting detectable light-pulses and correlating the reduction in measured light-pulses from said initially measured light-pulses to the reduction in the amount of antigens in said fluid linked to said two antibody-coated materials, and this correlative to the amount of unbound antibodies initially available in said fluid.

12. The method of claim 11 wherein said fluid is an aqueous medium having a pH in the range of about 6 and about 9, the temperature of said medium is between about 5° C. and about 40° C., and the concentration of said available antigens in said fluid medium is between about $10^{-5}$ M and about $10^{-12}$ M.

* * * * *